US00PP28568P2

(12) United States Plant Patent
Fitzgerald

(10) Patent No.: US PP28,568 P2
(45) Date of Patent: Oct. 24, 2017

(54) ***CAREX* PLANT NAMED 'EVERLITE'**

(50) Latin Name: *Carex oshimensis*
Varietal Denomination: Everlite

(71) Applicant: Garraith Ltd, Old Town (IE)

(72) Inventor: Pat Fitzgerald, Old Town (IE)

(73) Assignee: GARRAITH LTD, Stoneyford (IE)

( * ) Notice: Subject to any disclaimer, the term of this patent is extended or adjusted under 35 U.S.C. 154(b) by 31 days.

(21) Appl. No.: 14/998,802

(22) Filed: Feb. 17, 2016

(51) Int. Cl.
*A01H 5/12* (2006.01)

(52) U.S. Cl.
USPC ..... Plt./384

(58) Field of Classification Search
USPC ..... Plt./384, 373
See application file for complete search history.

*Primary Examiner* — June Hwu
(74) *Attorney, Agent, or Firm* — Penny J. Aguirre

(57) ABSTRACT

A new cultivar of *Carex oshimensis*, 'Everlite', characterized its foliage with white centers and green margins, its compact, dense growing habit, its foliage that is narrow in width, its foliage that is slightly twisted in aspect on young plants in the early stages of production and its ease of propagation.

2 Drawing Sheets

Botanical classification: *Carex oshimensis.*
Varietal denomination: 'Everlite'.

BACKGROUND OF THE INVENTION

The present invention relates to a new and distinct cultivar of *Carex oshimensis* and will be referred to hereafter by its cultivar name, 'Everlite'. 'Everlite' is a new cultivar of perennial ornamental grass grown for container and landscape use.

The new cultivar arose through an ongoing breeding and selection program conducted by the Inventor in Oldtown, Stoneyford, Co. Kilkenny, Republic of Ireland. The new cultivar arose from a proprietary screening protocol of plantlets produced by tissue culture. Through this process, 'Everlite' arose as a naturally occurring chimeral mutation of *Carex oshimensis* 'Evergold' (not patented). The Inventor selected 'Everlite' as a single unique plant in May of 2013.

Asexual propagation of the new cultivar was first accomplished by shoot division in December of 2013 in Oldtown, Stoneyford, Co. Kilkenny, Republic of Ireland. Asexual propagation by shoot division has determined that the characteristics are stable and are reproduced true to type in successive generations.

SUMMARY OF THE INVENTION

The following traits have been repeatedly observed and represent the characteristics of the new cultivar. These attributes in combination distinguish 'Everlite' as a distinct cultivar of *Carex.*

1. 'Everlite' exhibits variegated foliage with white centers and green margins.
2. 'Everlite' exhibits a compact, dense growing habit.
3. 'Everlite' exhibits foliage that is narrow in width (fine relative to typical cultivars of *Carex oshimensis*).
4. 'Everlite' exhibits foliage that is slightly twisted in aspect on young plants in the early stages of production.
5. 'Everlite' exhibits is very readily propagated.

'Evergold', the parent plant of 'Everlite', differs from 'Everlite' in having a more vigorous growth habit, in having variegated foliage with centers that are creamy-yellow in color, in having less dense growing habit and in having a larger mature plant size. 'Everlite' can be most closely compared to the cultivars 'CarFit01' (U.S. Plant Pat. No. 20,955) and 'Eversheen' (U.S. Plant Pat. No. 25,938). 'CarFit01' is similar to 'Everlite' in having variegated foliage that is white and green in color. 'CarFit01' differs from 'Everlite' in having a more vigorous habit, in having variegated foliage with centers that are green in color and edges that are white in color, and in having foliage that is less dense and lacks twisting. 'Eversheen' is similar to 'Everlite' in growth habit and growth rate. 'Eversheen' differs from 'Everlite' in having variegated foliage with green-yellow centers and in having foliage that is glossier and lacks twisting on young plants.

BRIEF DESCRIPTION OF THE DRAWINGS

The accompanying colored photographs illustrate the overall appearance and distinct characteristics of a one year-old plant the new *Carex* as field grown outdoors in Geldermalsen, The Netherlands and placed in a container for the photographs.

The photograph in FIG. 1 illustrates the plant habit and appearance of 'Everlite'.

Figure 1:
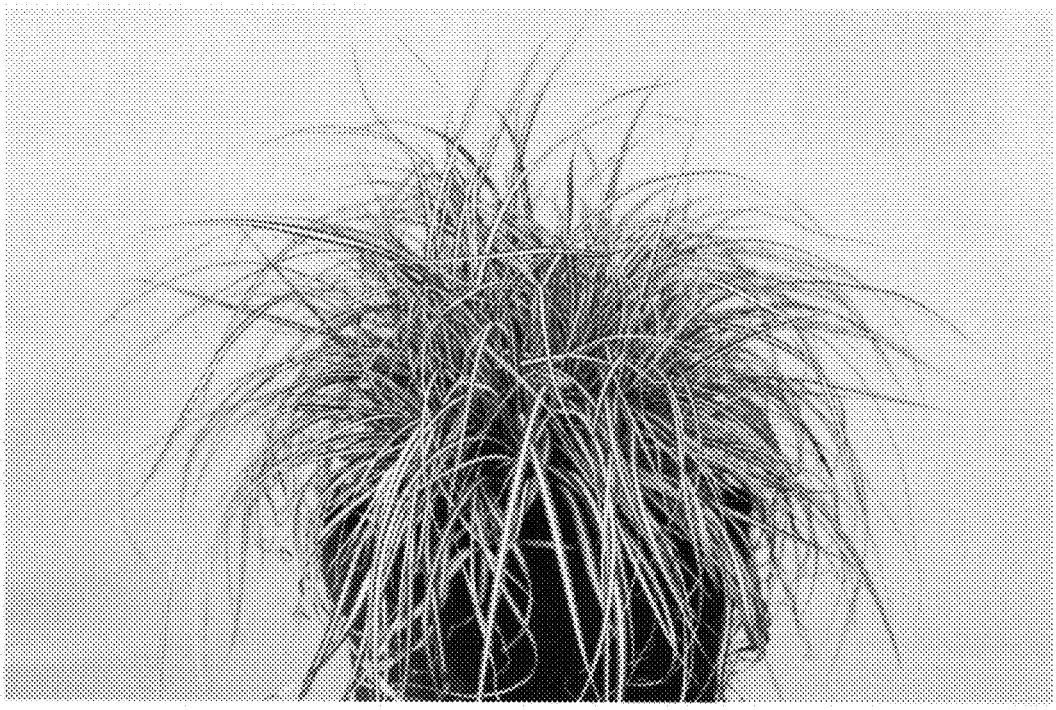
Figure 2:
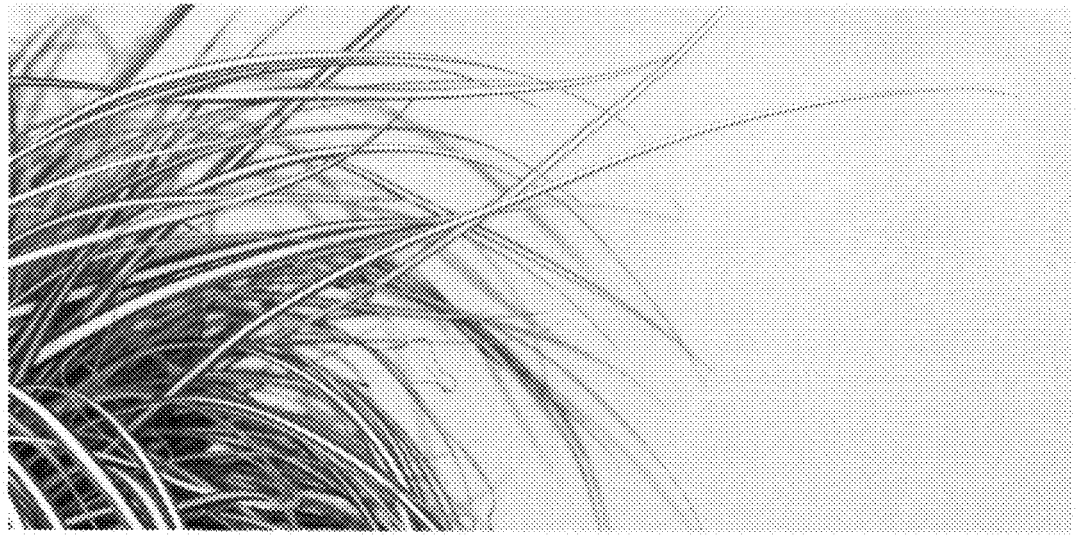

The photograph in FIG. 2 provides a close-up view of the foliage of 'Everlite'.

The colors in the photographs may differ slightly from the color values cited in the detailed botanical description, which accurately describe the colors of the new *Carex.*

DETAILED BOTANICAL DESCRIPTION

The following is a detailed description of one year-old plants as field grown outdoors in Geldermalsen, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—3 to 4 weeks from mid March to mid April in the Republic of Ireland.

*Plant habit.*—Herbaceous perennial, flattened globular with arching leaves and inflorescences.

*Growth habit.*—Broad, spreading.

*Height and spread.*—Average of 30 cm in height and 45 cm in diameter.

*Hardiness.*—At least in U.S.D.A. Zones 6.

*Growth rate.*—Moderate.

*Diseases and pests.*—No susceptibility or resistance to pests and diseases has been oberved.

*Root description.*—Short, stout rhizomes with dense, fibrous roots, roots moderately branched.

*Propagation.*—Shoot division.

*Propagation rate.*—An average of 12 shoots are produced from a single shoot division in about 3 months.

*Root development.*—A young plant will fully root in a liner in about 4 weeks.

*Shoots.*—An average of 53 main shoots growing from the base, base of shoot is triangular in shape.

*Growth rate.*—Moderate.

Foliage description:

*Leaf shape.*—Linear.

*Leaf division.*—Simple.

*Leaf base.*—Sheathing.

*Leaf apex.*—Long acuminate.

*Leaf aspect.*—Leaves initially emerge upright, then cascade outward and finally arch downward, young plants in production are twisted.

*Leaf venation.*—Parallel, upper surfaces striped NN155D and between 141A and 143A at the margins, lower surfaces striped NN155D, and between 143A and 191B and 191C at the margins.

*Leaf margins.*—Entire and moderately sharp when rubbed downwards due to very small teeth too small to be seen or measured.

*Leaf size.*—Average of 23.6 cm in length and 4.5 mm in width.

*Leaf number.*—Average of 8 leaves per shoot.

*Leaf arrangement.*—Alternate.

*Leaf surface.*—Upper surface slightly glossy and glabrous, lower surface moderately glossy and glabrous.

*Leaf color.*—Young upper surface; centers NN155D and broadly margined (about ⅓ of the leaf width on each side) with 143A to 143B, young lower surface; centers NN155D and broadly margined (about ⅓ of the leaf width on each side) with a blend of 143B, 191B and 191C, mature upper surface; centers NN155D and broadly margined (about ⅓ of the leaf width on each side) with a color between 141A and 143A, mature lower surface; centers NN155D and broadly margined (about ⅓ of the leaf width on each side) with a blend of 143A, 191B and 191C.

*Petiole.*—None.

*Leave sheathes.*—Average of 2.5 cm in length, 5 mm in width, surfaces are glabrous and 177C in color with stripes 177A.

Flower description:

*General description.*—Terminal racemes, male and female flowers on separate spikelets.

*Inflorescence size.*—Average of 6.5 cm in height and 1.8 cm in width.

*Flower quantity per inflorescence.*—Average of 45 male flowers placed on single spiklets and an average of 40 female flowers arranged in pairs of spikelets.

*Lastingness of inflorescence.*—Flowers last about 10 days.

*Response time to flower.*—Approximately 8 months.

*Rate of flower opening.*—After first initial flowers open in an inflorescence all flowers open within 3 weeks.

*Fragrance.*—None.

*Flower buds.*—Male flower: average of 0.5 cm in length and 2 mm in diameter, narrow oblong in shape and 199C in color, female flower: average of 0.5 cm in length and 2 mm in width, narrow obovate in shape and 147C in color.

*Spikelet shape.*—Sedge-like, narrowly ovate.

*Persistence of spikelets.*—Persistant.

*Floret (spikelet) size.*—Staminate florets; an average of 2 mm in diameter and 7 mm in length, pistillate florets; an average of 3 mm in diameter and 5 mm in length.

*Floret (spikelet) description.*—1 glume on inner side and 1 lemma on outer side, male flower: average of 1 glume and 1 lemma, glume and lemma surfaces smooth and dull, glume and lemma lanceolate in shape, glume and lemma entire margin, glume apex long, narrow and acute, lemma apex long mucronate, glume and lemma 8 mm in length and 1 mm in width, glume and lemma color: upper and lower surface when opening and fully open; N199C to N199D, female flower: (no glume), lemma; 1, smooth and dull surfaces, lanceolate in shape, entire margin, apex long mucronate, average of 5.5 mm in length and 1 mm in width, color: upper and lower surface when opening and fully open; 145A.

*Peduncle.*—An average of 22 cm in length and 1.5 mm in diameter, held nearly upright, strong, 145A in color.

Reproductive organs:

*Gynoecium.*—Average of 1 pistil about 3 mm in length, stigma is fimbriate and 156C in color, style is about 0.5 mm in length and 144A in color, ovary is 144D in color.

*Androcoecium.*—Average of 3 stamens, basifixed, about 2 mm in length and 162B in color, pollen production very low and insufficient in quantity to be color coded.

*Fruits and seeds.*—Seed production has not been observed to date.

It is claimed:

1. A new and distinct cultivar of *Carex* plant named 'Everlite' as herein illustrated and described.

* * * * *